(12) United States Patent
Wagner

(10) Patent No.: US 7,170,731 B2
(45) Date of Patent: Jan. 30, 2007

(54) CIRCUIT ARRANGEMENT FOR OPERATING A LINEAR EXHAUST GAS PROBE

(75) Inventor: Ekkehart-Peter Wagner, Bad Abbach (DE)

(73) Assignee: Siemens Aktiengesellschaft, Munich (DE)

( * ) Notice: Subject to any disclaimer, the term of this patent is extended or adjusted under 35 U.S.C. 154(b) by 499 days.

(21) Appl. No.: 10/689,963

(22) Filed: Oct. 21, 2003

(65) Prior Publication Data

US 2005/0072205 A1 Apr. 7, 2005

(30) Foreign Application Priority Data

Oct. 22, 2002 (DE) ................. 102 49 217

(51) Int. Cl.
*H02H 3/20* (2006.01)
*H02H 9/04* (2006.01)
*H02H 3/24* (2006.01)

(52) U.S. Cl. ..................... 361/91.1; 361/90
(58) Field of Classification Search .......... 361/91.1, 361/90
See application file for complete search history.

(56) References Cited

U.S. PATENT DOCUMENTS 4,046,118 A * 9/1977 Aono .............. 123/683

5,211,820 A * 5/1993 Poor et al. ............ 205/784.5

FOREIGN PATENT DOCUMENTS

DE 101 01 755 C1 7/2002

* cited by examiner

*Primary Examiner*—Stephen W. Jackson
*Assistant Examiner*—Dharti H. Patel
(74) *Attorney, Agent, or Firm*—Baker Botts L.L.P.

(57) ABSTRACT

A circuit arrangement for operating a sensor comprises a control circuit for electrically supplying the sensor via a plurality of connecting lines and/or at least to detect one electrical output signal of the sensor in which case one of the connecting lines is routed via one actuatable switching element that is suitable for interrupting this line, and to detect the potential on at least one of the connecting lines and should an abnormal potential be detected on this connecting line, to actuate the switching element for interrupting the connecting line. Furthermore, one actuatable further switching element is provided for connecting a pair of connecting lines and the circuit arrangement is designed in such a way that it can actuate the connection of these connecting lines, should an abnormal potential of this further switching element be detected, to break down a potential difference between connections of the sensor.

19 Claims, 2 Drawing Sheets

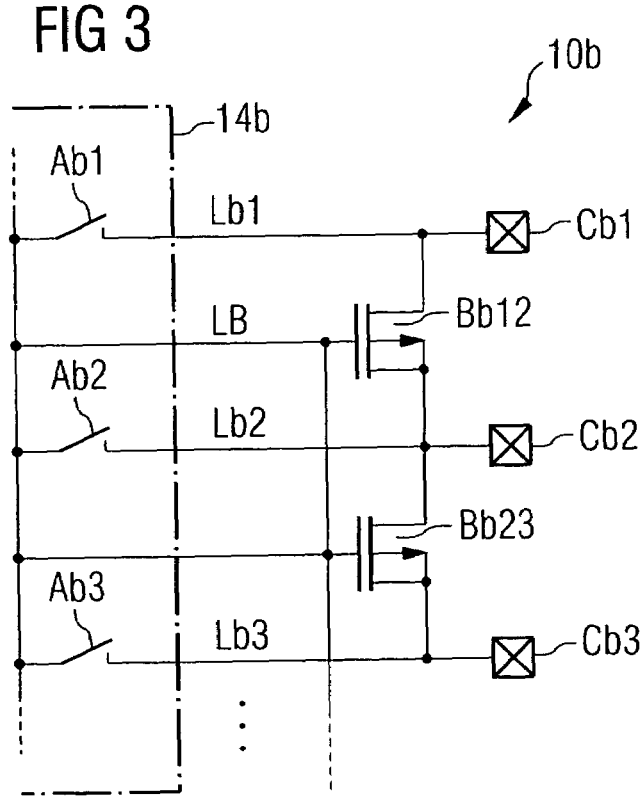
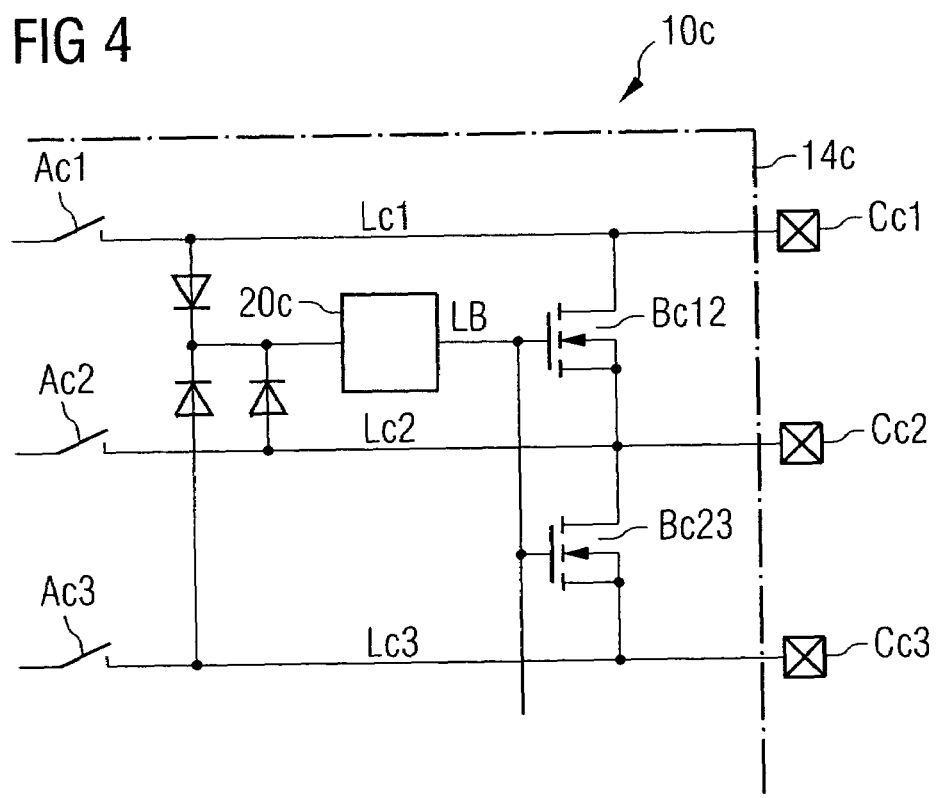

CIRCUIT ARRANGEMENT FOR OPERATING A LINEAR EXHAUST GAS PROBE

PRIORITY

This application claims foreign priority of the German application DE 10249217.4 filed on Oct. 22, 2002.

TECHNICAL FIELD

This invention relates to a circuit arrangement for operating a sensor, in particular, a circuit arrangement for a linear exhaust gas sensor for an internal combustion engine ("lambda probe").

BACKGROUND OF THE INVENTION

Of particular interest for the invention are, in general, all types of sensors in which an excessively high voltage between the connections of the sensor bring about the danger of impairing the sensor function and/or the danger of irreversible damage to the sensor. This is, for example, the case for many gas sensors in which operational voltages are applied to a ceramic material via the sensor connections or currents are allowed to flow through this ceramic material. Such sensors can be impaired or damaged if too high voltages are applied to the ceramic material. Therefore, measures have usually been taken for well-known circuit arrangements to operate such sensors to avoid the occurrence of excessively high voltages at critical points of the sensor.

A circuit arrangement with the features of the preamble of claim 1 is well-known. In the case of this well-known circuit arrangement for operating a linear exhaust gas sensor for an internal-combustion engine, a control circuit is provided to supply the exhaust gas sensor via a plurality of connecting lines with an electrical pump current and to detect this pump current as well as a sensor voltage as electrical output signals of the exhaust gas sensor. In order to protect the exhaust gas sensor from destruction by applying a disproportionately high voltage at a pump cell loaded with a pump current as well as at the sensor, the control circuit detects an electrical potential at the connecting lines by means of comparators and, in the case of a disproportionately high voltage, activates the switching transistors to interrupt the connecting lines. Such impermissibly high voltages can, for example, occur in the case of a short-circuit with a voltage-carrying line situated in the vicinity and without this controlled interruption of the connecting lines could damage the pump cell or sensor of the exhaust gas probe.

However, damage to the sensor is not totally excluded even when this known circuit arrangement is used. On the one hand, this known suppressor circuit is only effective in operation because after the supply voltage has been switched off, abnormal potentials are not detected and there might be no interruption of the connecting lines. In the case of a motor vehicle that uses the known circuit arrangement to operate an exhaust gas sensor, the above-mentioned interruption function is no longer provided after, for example, the engine of the motor vehicle has been switched off. Even when the circuit arrangement is in operation, optimum protection is not available because the switching transistors used to interrupt the connecting lines have a finite electrical resistance even in the opened state so that, depending on the type of overvoltage applied, there may still be an impermissibly high voltage at the sensor. This problem is all the more serious, the greater the internal resistance of the sensor between the relevant sensor connections, since an abnormal potential occurring in the area of the connecting lines in the case of a high internal sensor resistance drops off at this very internal resistor. As is well-known, a ceramic material (e.g. zirconium ceramic) used to construct a linear exhaust gas probe has a resistance that strongly depends on the temperature. In the cold state of the sensor, e.g. immediately after starting the internal-combustion engine, the internal resistances of the sensor developed by the ceramic materials are extremely high so that even small leakage currents flowing over the switching transistors can give rise to particularly high voltage drops at the sensor.

SUMMARY OF THE INVENTION

Accordingly, one object of this invention is to provide a circuit arrangement of the type mentioned at the beginning that reliably protects a connected sensor against impairment or destruction by applying a high voltage and a method for operating such a sensor.

This object of the invention can be achieved by a circuit arrangement for operating a sensor, in particular, a circuit arrangement for a linear exhaust gas sensor for an internal combustion engine, comprising a control circuit that is designed to electrically supply the sensor via a plurality of connecting lines and/or at least to detect one electrical output signal of the sensor in which case one of the connecting lines is routed via one actuatable switching element that is suited to interrupt this line, and in which case the circuit arrangement is designed to detect the potential on at least one of the connecting lines and, should an abnormal potential be detected on this connecting line, to actuate the switching element for interrupting the connecting line, and at least one actuatable further switching element that is suitable for connecting a pair of the connecting lines, wherein the circuit arrangement is designed in such a way that it can actuate the connection of these connecting lines should an abnormal potential of this further switching element be detected to break down a potential difference between the connections of the sensor.

The object can also be achieved by a circuit arrangement for operating a sensor, in particular, a circuit arrangement for a linear exhaust gas sensor for an internal combustion engine, comprising a control circuit for electrically supplying the sensor via a plurality of connecting lines and/or at least for detecting one electrical output signal of the sensor, an actuable switching element controlled by the control circuit for routing one of the connecting lines, a detector for detecting the potential on at least one of the connecting lines coupled with the switching element for actuating the switching element for interrupting the connecting line, and at least one actuatable further switching element for connecting a pair of the connecting lines, wherein the circuit arrangement is designed in such a way that it can actuate the connection of these connecting lines should an abnormal potential of this further switching element be detected to break down a potential difference between the connections of the sensor.

The object can further be achieved by a method for operating a sensor, in particular, a linear exhaust gas sensor for an internal combustion engine, comprising the steps of:

supplying the sensor electrically via a plurality of connecting lines and/or at least detecting one electrical output signal of the sensor in which case one of the connecting lines is routed via one actuatable switching element that is suited to interrupt this line, and in which case the circuit arrangement is designed to detect the potential on at least one of the connecting lines and, should an abnormal potential be detected on this connecting line, actuating the switching element for interrupting the connecting line, and actuating the connection of a pair of connecting lines via an actuable further switching element should an abnormal potential of this further switching element be detected to break down a potential difference between the connections of the sensor.

A number of the connecting lines can be routed via a switching element that can be actuated and that is suitable for interrupting the relevant connecting line and, should an abnormal potential be detected, these switching elements are at the same time actuated to interrupt the relevant connecting lines. An actuatable further switching element can be provided in each case between a number of pairs of the connecting lines that is suitable for connecting the corresponding connecting lines in pairs, and should an abnormal potential be detected, these further switching elements are at the same time actuated to connect the relevant connecting lines. At least one of the switching elements and/or further switching elements can be designed as a channel of a transistor. At least one of the further switching elements can be operated wattless to connect the two connecting lines. At least one of the further switching elements can be actuated to connect the two connecting lines by means of an actuating circuit which provides an actuating potential for actuating purposes and is applied to a control input of the switching element, and in which case this actuating circuit is connected to a number of connecting lines to be supplied with the abnormal potential when an abnormal potential occurs on one of these connecting lines. The control circuit as well as the switching elements and further switching elements can be united in an integrated circuit.

Of considerable importance for the invention is the fact that in addition to an interruption of the line connection between the actuating circuit and the connected sensor, at least one pair of connecting lines are connected to one another to break down a potential difference between the relevant sensor connections. As a matter of course, this electrical connection should have the lowest impedance possible, perhaps as a short-circuit connection so that a destructively high potential difference can no longer develop at the connected sensor. The advantage of the solution according to the invention is that by arranging connecting switching elements that can be actuated, cross currents through the sensor can be avoided that, in particular, for high impedance internal sensor resistances, could lead to particularly high and, therefore, destructive potential differences.

In the simplest case, the sensor is connected to the control circuit via two connecting lines of which one, when detecting an abnormal potential on any one of the two lines, is interrupted by a switching element (interruption switching element) in which case a further switching element (connecting switching element) establishes a low impedance connection between the two lines in this case.

More complicated sensors designs need more than two connecting lines to supply or detect one or more sensor output signals of which, according to the invention, at least one is provided with a switching element that can be actuated (interruption switching element) and at least one further switching element that can be actuated (connecting switching element) for connecting two lines is provided. Which one of the a number of connecting lines should be provided with an interruption switching element and which one of these connecting lines should be connected with one another in pairs, if required, depends on the actual design of the sensor. In general, it would be practical, when detecting an abnormal potential on any one of the connecting lines to at least interrupt all those connecting lines between which the sensor has a range that is oversensitive to the voltage and connect them with one another.

Therefore, it is preferred in many applications if a number of connecting lines are routed via an interruption switching element that can be actuated and that is suited to interrupt the specific connecting line and, should an abnormal potential be detected, these switching elements are at the same time actuated to interrupt the relevant connecting lines and/or should a connecting switching element that can be actuated be provided between a number of pairs of connecting lines which is suitable for connecting the corresponding connecting lines in pairs, and should an abnormal potential be detected, these connecting switching elements are actuated at the same time to connect the relevant connecting lines. Therefore, in particular, all the connecting lines can then be interrupted and connected with one another. The latter embodiment even has the advantage that the protection function of the line connection is universal, i.e. guaranteed separately from the actual sensor used.

In a particularly preferred form of embodiment, at least one of the interruption switching elements and/or connecting switching elements, especially the totality of these interruption switching elements and connecting switching elements, is designed as an electronic switch, especially as the channel of a transistor. The term "channel" refers here to a transistor path whose resistance can be changed depending on an actuating potential that is applied to the control input of the transistor, therefore, the source drain path of a field effect transistors (FET) or the emitter collector path of a bipolar transistor.

In a further development of the invention, the circuit arrangement is designed in such a way that, should there be no power supply to the circuit arrangement, the interruption switching elements provide an interruption and/or the connecting switching elements a connection. Both measures reduce the danger of damage to the sensor due to an overvoltage even in the case of an inactive (not-supplied) circuit arrangement. For example, at least one of the connecting switching elements, particularly each one of the connecting switching elements, can be designed wattless to connect the two connecting lines in an operable way. When implementing these switching elements with transistors, self-conducting FETs can, for example, be provided.

In a further embodiment of the invention, provision is made for at least one of the connecting switching elements to be actuated to connect two connecting lines by means of an actuating circuit which provides an actuating potential for actuating purposes and is applied to a control input of the connecting switching element, and whereby this actuating circuit is connected to a number of connecting lines to be supplied with the abnormal potential when an abnormal potential occurs on one of these connecting lines. This measure has a surprising advantage. On the one hand, the effectiveness of the overvoltage protection can also be obtained when the power supply of the circuit arrangement is switched off, whereby, on the other hand, the connecting elements to be actuated can be used actively for connecting the two connecting lines, i.e. with a more or less high actuating output, because the output required to actuate these switches is obtained from the abnormal potential itself. Therefore, switches can, in particular, be used that have a particularly low impedance in the connected-through state. Useful for this embodiment is the actuating circuit connected to all the connecting lines that should be connected to another connecting line in the case of an overvoltage. In this way, it is ensured that each potential difference occurring between the connecting lines to be connected, i.e. in particular, every overvoltage that is dangerous under the circumstances can be used by the actuating circuit.

However, in the latter form of embodiment, depending on the actual type of connecting switching elements, the problem can result that an actuating potential required for actuating a connecting switching element cannot simply be "tapped" via the actuating circuit of the connecting lines. This problem can e.g. occur when using self-blocking FETs as connecting switching elements. This is explained by way of an example. If two connecting lines are short-circuited with low impedance via the source drain path of such an FET when there is a potential difference between these two connecting lines, the potentials at the source and drain will adapt to one another, so that in this case an actuating potential is required at the gate of the FET for maintaining the low impedance that lies outside the potential range defined by the two potentials on the connecting lines.

This problem can be solved within the framework of the invention by for example providing a known voltage multiplier as part of the actuating circuit that can be used to serve as an actuating potential lying outside the range defined by the tapped line potentials. Suitable voltage multipliers, sometimes also referred to as the "booster" or "charge pump" are sufficiently known and, therefore, need not be described in detail here. A functional principle known for a booster in an integrated circuit consists for example of applying, during a first phase, a clock signal of a first connection of a transfer capacitor generated by a clock at a supply potential, whereby during a second phase of the clock signal the first connection is disconnected from the supply potential by means of an electronic switch and a second connection of the same capacitor is connected to earth and a second connection is disconnected from earth and connected to the supply potential. The potential prevailing at the first connection of the transfer capacitor is then above the supply potential and can, for example, be used to charge a charge storage capacitor to provide the output potential of the booster continuously and is even capable of being charged.

The circuit arrangement can be provided with a number of such actuating circuits that in each case supply one of a number of connecting switching elements with the actuating potential needed for connecting. If a number of connecting switching elements are provided, it is however preferred that such an actuating circuit actuates a number of connecting switching elements at the same time for connecting the relevant connecting lines. This idea of jointly actuating a number of connecting switching elements does not depend on the arrangement of an "autonomous" actuating circuit and can, for example, also be implemented by the control circuit when actuating the connecting switching elements. For example, a number of connecting switching elements can in each case be embodied as a channel of an FET in which case gate terminals connect several of these FETs with one another and are connected to the control circuit via a further (actuating) connecting line.

Advantageously, some or all the components of the circuit arrangement can be combined into an integrated circuit in a simple and cost-effective way, e.g. into an application-specific integrated circuit (ASIC). In particular, the control circuit as well as the interruption switching elements and the connecting switching elements can be combined into an integrated circuit.

In a further development of the invention, the circuit arrangement is designed in such a way that on detection of an abnormal potential, fault diagnosis can be carried out that is helpful with regard to eliminating the source of the fault. In order to increase the reliability of such a fault diagnosis it is favorable if there is a short period of time between the occurrence of the abnormal potential and activation of the connecting switching elements that is sufficient to detect information about the fault quite accurately, for example, via the control circuit. This can be obtained by an arrangement of an appropriately designed delay circuit, either when the connecting switching elements are actuated via the control circuit or when these connecting switching elements are actuated by an actuating circuit that is independent from these. The fault information can, for example, be detected digitally during the delay time.

BRIEF DESCRIPTION OF THE DRAWINGS

The invention is described in more detail below using exemplary embodiments which refer to the drawings provided. The drawings show.

DETAILED DESCRIPTION OF THE PREFERRED EMBODIMENTS

Figure 1:
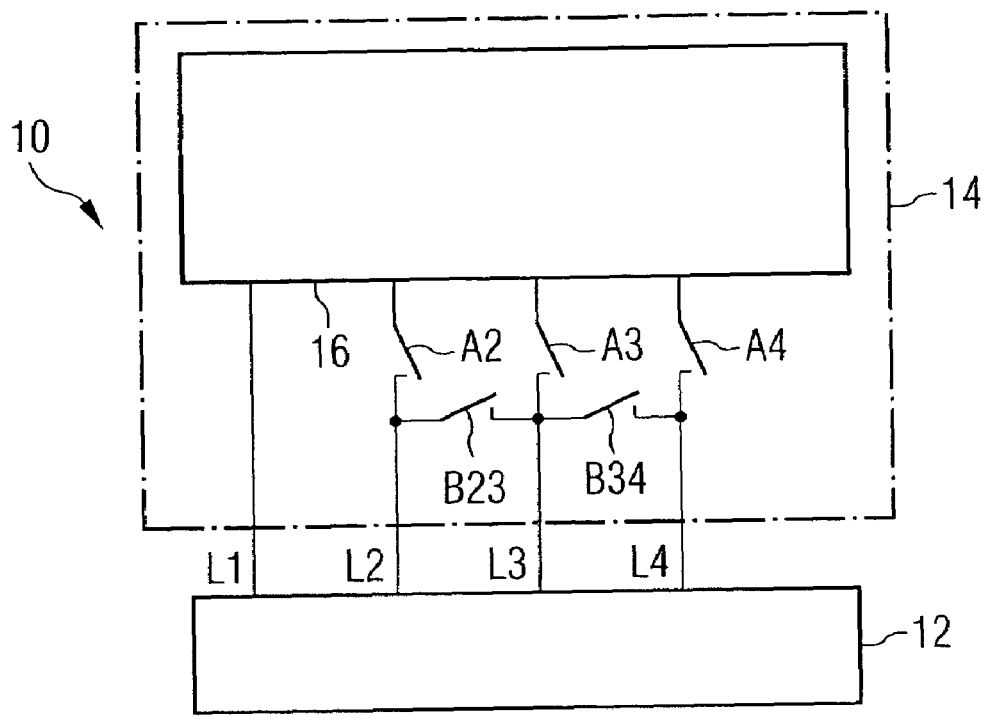
FIG. 1 a wiring diagram of a circuit arrangement together with a sensor operated by it according to a first embodiment, FIG. 2 a wiring diagram of a circuit arrangement together with a sensor operated by it according to a second embodiment, FIG. 3 a wiring diagram of the detail of a circuit arrangement according to a third embodiment, and FIG. 4 a wiring diagram of the detail of a circuit arrangement according to a fourth embodiment.

FIG. 1 shows a circuit arrangement designated collectively as 10 for operating an overvoltage-sensitive sensor 12, whereby the circuit arrangement 10 in this example is an integrated circuit that is symbolized in FIG. 1 by a broken line 14.

Circuit arrangement 10 has a control circuit 16, electrically supplying sensor 12 and by means of which electrical output signals of sensor 12 are detected and processed further in non-displayed switching parts of the integrated circuit 14. In this case, the sensor 12 is connected to the control circuit 16 via connecting lines L1, L2, L3, and L4. All these connecting lines are also designated with an L below.

The lines L2, L3, L4 are routed via actuatable, electronic switching elements A2, A3, A4 (in general also referred to as A below) suitable for interrupting these lines L2, L3, L4, that are closed during normal operation to enable orderly operation of the sensor 12.

The control circuit 16 monitors the potentials on the lines L and actuates the switches A2, A3, A4 to interrupt the lines L2, L3, L4 if one of the monitored potentials is evaluated as "abnormal", and therefore has a value that is outside a potential range to be expected during operation for the relevant line. In the exemplary embodiment shown the potentials on all the lines L are compared by means of non-displayed comparators to one or two limiting potentials in each case to determine whether or not there is an abnormal potential on any one of the lines L, therefore, an excessively low or high potential. In this way, the case is established in which, between connections of the sensor a voltage is applied that brings with it the danger of impairment or damage to the sensor. This case, also referred to as the fault case below can, for example, occur because of a short-circuit of one of the lines L triggered by another voltage-carrying line located in the vicinity. if this type of fault is detected, control circuit 16 analyses the potentials prevailing on lines L with regard to a fault diagnosis and then actuates switches A2, A3, A4 to interrupt the relevant lines L2, L3, L4 so that sensor 12 is isolated to a large extent and damage to sensor 12 by the abnormal potential is prevented.

In the exemplary embodiment shown, a break switch in line L1 is dispensed with because the area of sensor 12 connected with this line is non-sensitive to possibly occurring overvoltages. On the other hand, in the example shown, the sensor areas between the lines L2 and L3 as well as between the lines L3 and L4 are insulated by these actively actuated line interruptions in case a fault occurs.

However, this protection of sensor 12 against overvoltages is not perfect because interruption switches A2, A3, A4 also have a finite resistance in the open state according to FIG. 1 or can conduct a non-disappearing leakage current so that the isolation of sensor 12 realized in this way is sometimes insufficient to protect this sensor against impairment. For this reason, there are further electronic switches (connecting switches) B23, B34 (also generally designated as below B) arranged on the sensor side between lines L2 and L3 or L3 and L4 that are, if a fault occurs, at the same time actuated with the above-mentioned interruption switches A via the control circuit 16 to short-circuit the lines L2, L3, L4 to each other. In the simplest case, these connecting switches B are designed in the same way as the interruption switches A, for example each as a channel of a transistor for which the resistance can be changed by varying an actuating potential at a gate terminal of the transistor. As a result of this low impedance connection of the lines L2, L3, L4 resulting if an abnormal potential is detected on one of the lines L, a potential difference can be set up rapidly in this area of sensor 12. This advantageous action of switch B is already significant when possible leakage currents flowing over the lines L essentially flow over switches B instead of as cross currents inside sensor 12. In other words it will in general suffice if the resistance of switches B is in the order of magnitude of the internal resistances of the sensor 12 or even smaller.

In the description of further exemplary embodiments below, the same reference symbols are used for similar components, in each case supplemented by a smaller letter to distinguish the form of embodiment. In essence, only the differences from the exemplary embodiment or embodiments already described are dealt with here and reference is expressly made here to the description of previous exemplary embodiments.

Figure 2:
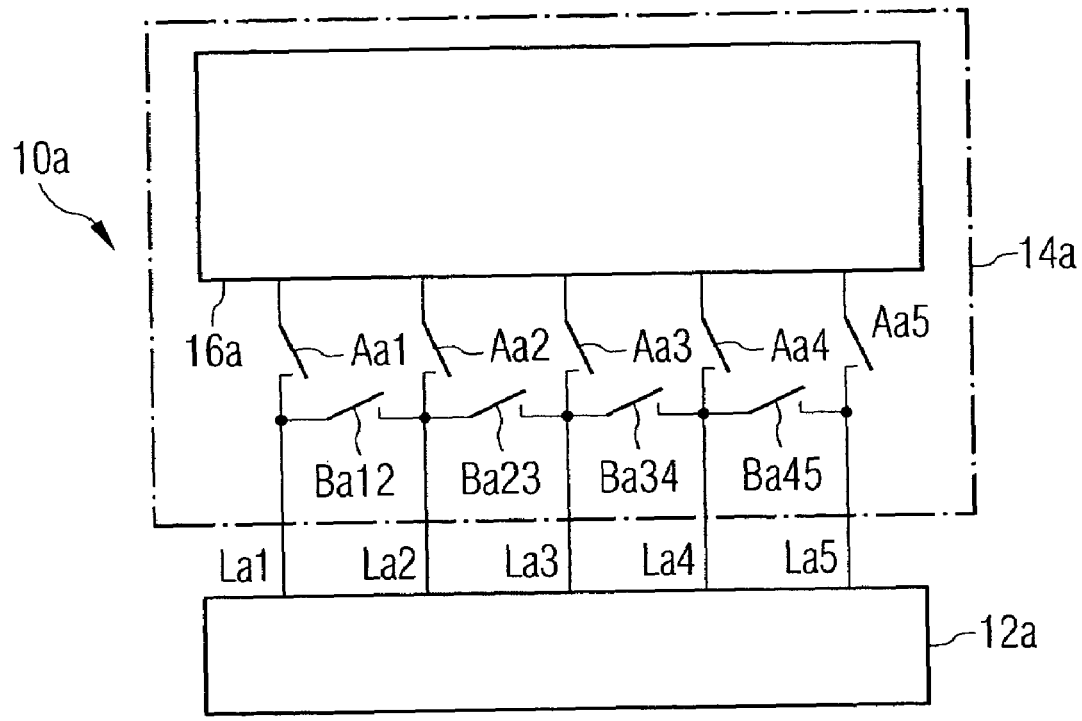

FIG. 2 shows a further exemplary embodiment of a circuit arrangement 10a, including a control circuit 16a as well as a series of connecting lines La1 to La5 for operating a linear exhaust gas probe (lambda probe) 12a for the internal combustion engine of a motor vehicle. In the case of this known probe, a first electrode pair is arranged between a detection chamber and the surrounding air and is used to measure the concentration of oxygen in this detection chamber by measuring a Nernst voltage triggered by a difference in the gas concentration at these measuring electrodes by means of the control circuit 16a. The detection chamber together with the measuring electrode arrangement forms the so-called sensor. A second electrode pair is arranged between the detection chamber and the exhaust gas flow and, when an electrical current of the appropriate polarity is applied, allows oxygen ions to be pumped from or into the detection chamber. For this purpose, the detection chamber is connected to the exhaust gas flow via a diffusion barrier made of zirconium ceramics. This diffusion barrier forms the so-called pump cell together with the pump electrodes.

During operation of this known probe 12a, a dynamic balance is set between oxygen flows determined by the diffusion and pump current from and into the detection chamber by a corresponding regulation of the pump current provided by the control circuit 16a. A suitable regulating criterion here is the oxygen concentration in the detection chamber determined by the measuring electrodes. This concentration, for example, can be regulated at a value corresponding to a specific air/fuel ratio of $\lambda=1$ with a Nernst voltage (sensor voltage) of typically approximately 450 mV. The pump flow though the pump cell in this case is then a measurement for the oxygen concentration in the exhaust gas or (after numerical conversion) a measurement for the air/fuel ratio which is of interest.

A circuit arrangement by means of which a linear lambda probe can be operated in this way is known, for example, from the German patent specification DE 101 01 755 C1.

In order to bring the probe 12a to its nominal operating temperature in a range of typically approximately 500° C. to 800° C. after the internal combustion engine has started or to also explicitly set the probe temperature, the probe 12a is provided with a heating installation specifically provided for this purpose that is also operated via the connecting lines La.

Depending on the ceramic material used for the pump cell, should a pump voltage of approximately 2V to 3V be exceeded, the probe function will be impaired and there will also be irreversible damage to probe 12a and indeed by a so-called "blackening" or formation of cracks on the material of the fixed electrolytes used in the pump cell. The occurrence of such an excessively large pump voltage is prevented during normal operation by the fact that the source of the pump current provided in the circuit arrangement 10a is designed from the start with a correspondingly restricted output voltage range that prevents the probe 10a from being damaged. However, to be able to protect the sensor 12a from destruction by applying an overvoltage in case of a fault of a short-circuit between one of the lines La and a voltage-carrying line of the electrical system of the motor vehicle, electronic switches Aa1 to Aa5 that can be actuated are again provided by means of which, in the case of such a fault, all the connecting lines La are interrupted to prevent damage to an abnormal, i.e. excessively small or large potential on one of the lines La. However, because the switches Aa that are open in case of a fault do not have an infinitely large electrical resistance, the control circuit 16a in this case, at the same time, actuates further actuatable electronic switches Ba12, Ba23, Ba34 and Ba45 for the low impedance connection of all the connecting lines La with one another to rapidly break down all the potential differences between the connections of the probe 12a. In the same way as for the exemplary embodiment described with reference to FIG. 1, the interruption switches Aa as well as the connecting switches Ba are implemented together with the control circuit 16a in an integrated circuit 14a.

FIG. 3 shows the detail of a further circuit arrangement 10b in which the interruption switches Ab are combined with the control circuit into an integrated circuit 14b, however, the connecting switches Bb (designed as self-conducting p-channel FETs) are arranged outside this integrated circuit 14b, for example, in a further integrated circuit that in this case can also be arranged in the vicinity of the sensor (not shown in FIG. 3).

During normal operation of the sensor, the interruption switches Ab also implemented as transistors are closed and the connecting switches Bb opened. The high impedance of the channels of these electronic switching elements Bb is achieved by applying an actuating potential at the gate terminals of transistors Bb suited for blocking these transistors. For this purpose, the gate terminals of transistors Bb are interconnected and connected to the control circuit of the circuit arrangement 10*b* via a common actuating line LB.

In case of a fault, therefore if the control circuit on one of the monitored lines Lb detects an abnormal potential, the interruption switches Ab are actuated to interrupt the lines Lb and the connecting switches Bb are actuated via the actuating line LB for the low impedance connection of the lines Lb in pairs. The sensor (not shown) is connected to the connections Cb seen in FIG. 3 on the right-hand side.

In addition to the advantage of a rapid and reliable break down of potential differences, a further advantage of this embodiment is the fact that, should the circuit arrangement 10*b* be switched off (for example, application of a lambda probe when the vehicle is switched off), the connecting switches Bb will be closed in which case both the connected sensor and the inactive circuit arrangement 10*b* will be protected effectively. When commissioning the circuit arrangement 10*b*, the connecting switches B are opened immediately and remain open for as long as the control circuit does not detect an abnormal potential.

FIG. 4 shows a further exemplary embodiment of a circuit arrangement 10*c* in which the interruption switches Ac are again combined with the connecting switches Bc in an integrated circuit 14*c* that can be connected to a sensor (not shown) via connecting contacts Cc. Deviating from the embodiment described previously with reference to FIG. 3, the connecting switches Bc are embodied as self-blocking n channel FETs here and, therefore, have a high impedance should the control circuit be inactive. Nevertheless, the circuit arrangement 10*c* also offers an effective overvoltage protection in this case because the transistors Bc are actuated to connect two of the connecting lines Lc in pairs in each case by means of an actuating circuit, that is formed here from a voltage multiplier 20*c* as well as a number of diodes and, on the output side, provide the actuating potential required to actuate the transistors Bc and is applied via an actuating line LB to the gate terminals of the transistors Bc. Because of the connection of the voltage multiplier 20*c* on the input side (via the diodes) to a number of lines Lc, the voltage multiplier 20*c* is self supplied should an abnormal potential occur on one of these lines Lc. The diodes then galvanically separate the relevant lines Lc. In a way known per se, the voltage multiplier 20*c*, in the case of a fault, then generates an actuating potential on the actuating line LB, which lies outside the potential range defined by the potentials on the connected lines Lc and is suited for the reliable through connection of transistors Bc.

Even in the case of circuit arrangement 10*c*, it is conceivable to provide the connecting transistors Bc together with their autonomous actuating circuit outside the integrated circuit 14*c*. As shown in FIG. 4 and deviating from the advantageous actuation of a number of connecting switches Bc by a common voltage multiplier 20*c* it is naturally also possible to arrange a separate voltage multiplier for the individual connecting switches in each case.

To sum up, the invention provides a protective circuit for sensors for which at least parts of the sensor are overvoltage-sensitive, whereby the sensor can be protected reliably against overvoltages occurring in case of a fault. Of particular interest is the application of the invention, for example, for sensors in a more or less "rough" environment with a higher probability for the occurrence of the fault situation described above, such as sensors in a motor vehicle. Here, it can, for example, be an exhaust gas sensor (for example, for $NO_x$, $O_2$ etc.). Impairment of the sensor function that can be prevented with the invention is of particular importance for linear exhaust gas sensors that are usually used for a particularly precise exhaust gas concentration measurement (for example, a linear lambda probe). Of course, other areas of application are not excluded (e.g. industrial gas sensors).

Although the electronic switching elements used are described as FETs in the exemplary embodiments, this must only to be considered as giving typical examples. Naturally, bipolar transistors or comprehensive transistor arrangements with a number transistors in each case can be used instead (for example, a complementary FET pair with combined source connections and combined drain connections).

The invention claimed is:

1. A circuit arrangement for operating a sensor, in particular, a circuit arrangement for a linear exhaust gas sensor for an internal combustion engine, comprising:
    a control circuit that is designed to electrically supply the sensor via a plurality of connecting lines and/or at least to detect one electrical output signal of the sensor in which case one of the connecting lines is routed via one actuatable switching element that is suited to interrupt this line, and in which case the circuit arrangement is designed to detect the potential on at least one of the connecting lines and, should an abnormal potential be detected on this connecting line, to actuate the switching element for interrupting the connecting line,
    at least one actuatable further switching element that is suitable for connecting a pair of the connecting lines, wherein the circuit arrangement is designed in such a way that it can actuate the connection of these connecting lines should an abnormal potential of this further switching element be detected to break down a potential difference between the connections of the sensor.

2. The circuit arrangement according to claim 1, wherein a number of the connecting lines are routed via a switching element that can be actuated and that is suitable for interrupting the relevant connecting line and, should an abnormal potential be detected, these switching elements are at the same time actuated to interrupt the relevant connecting lines.

3. The circuit arrangement according to claim 1, wherein an actuatable further switching element is provided in each case between a number of pairs of the connecting lines that is suitable for connecting the corresponding connecting lines in pairs, and should an abnormal potential be detected, these further switching elements are at the same time actuated to connect the relevant connecting lines.

4. The circuit arrangement according to claim 1, wherein at least one of the switching elements and/or further switching elements are designed as a channel of a transistor.

5. The circuit arrangement according to claim 1, wherein at least one of the further switching elements can be operated wattless to connect the two connecting lines.

6. The circuit arrangement according to claim 1, wherein at least one of the further switching elements is actuated to connect the two connecting lines by means of an actuating circuit which provides an actuating potential for actuating purposes and is applied to a control input of the switching element, and in which case this actuating circuit is connected to a number of connecting lines to be supplied with the abnormal potential when an abnormal potential occurs on one of these connecting lines.

7. The circuit arrangement according to claim 1, wherein the control circuit as well as the switching elements and further switching elements are united in an integrated circuit.

8. A method for operating a sensor, in particular, a linear exhaust gas sensor for an internal combustion engine, comprising the steps of:
supplying the sensor electrically via a plurality of connecting lines and/or at least detecting one electrical output signal of the sensor in which case one of the connecting lines is routed via one actuatable switching element that is suited to interrupt this line, and in which case the circuit arrangement is designed to detect the potential on at least one of the connecting lines and, should an abnormal potential be detected on this connecting line, actuating the switching element for interrupting the connecting line,
actuating the connection of a pair of connecting lines via an actuable further switching element should an abnormal potential of this further switching element be detected to break down a potential difference between the connections of the sensor.

9. The method according to claim 8, wherein a number of the connecting lines are routed via a switching element that can be actuated and that is suitable for interrupting the relevant connecting line and, should an abnormal potential be detected, these switching elements are at the same time actuated to interrupt the relevant connecting lines.

10. The method according to claim 8, further comprising the step of providing an actuatable further switching element in each case between a number of pairs of the connecting lines that is suitable for connecting the corresponding connecting lines in pairs, and should an abnormal potential be detected, actuating these further switching elements are at the same time to connect the relevant connecting lines.

11. The method according to claim 8, comprising the step of operating at least one of the further switching elements wattless to connect the two connecting lines.

12. The method according to claim 8, comprising the step of actuating at least one of the further switching elements to connect the two connecting lines by means of an actuating circuit which provides an actuating potential for actuating purposes and is applied to a control input of the switching element, and in which case connecting this actuating circuit to a number of connecting lines to be supplied with the abnormal potential when an abnormal potential occurs on one of these connecting lines.

13. A circuit arrangement for a linear exhaust gas sensor for an internal combustion engine comprising:
a control circuit for electrically supplying the sensor via a plurality of connecting lines and/or at least for detecting one electrical output signal of the sensor,
a first actuable switching element controlled by the control circuit for routing one of the connecting lines,
a detector for detecting the potential on at least one of the connecting lines coupled with the first switching element for actuating the switching element for interrupting the connecting line,
a second switching element for connecting a pair of the connecting lines, wherein the circuit arrangement controls the connection of the connecting lines in response to a detected abnormal potential of the second switching element be detected to break down a potential difference between the connections of the sensor.

14. The circuit arrangement according to claim 13, wherein a number of the connecting lines are routed via a switching element that can be actuated and that is suitable for interrupting the relevant connecting line and, should an abnormal potential be detected, these switching elements are at the same time actuated to interrupt the relevant connecting lines.

15. The circuit arrangement according to claim 13, wherein an actuatable further switching element is provided in each case between a number of pairs of the connecting lines that is suitable for connecting the corresponding connecting lines in pairs, and should an abnormal potential be detected, these further switching elements are at the same time actuated to connect the relevant connecting lines.

16. The circuit arrangement according to claim 13, wherein at least one of the switching elements and/or further switching elements are designed as a channel of a transistor.

17. The circuit arrangement according to claim 13, wherein at least one of the further switching elements can be operated wattless to connect the two connecting lines.

18. The circuit arrangement according to claim 13, wherein at least one of the further switching elements is actuated to connect the two connecting lines by means of an actuating circuit which provides an actuating potential for actuating purposes and is applied to a control input of the switching element, and in which case this actuating circuit is connected to a number of connecting lines to be supplied with the abnormal potential when an abnormal potential occurs on one of these connecting lines.

19. The circuit arrangement according to claim 13, wherein the control circuit as well as the switching elements and further switching elements are united in an integrated circuit.

* * * * *